United States Patent [19]

Chu et al.

[11] Patent Number: 4,725,671
[45] Date of Patent: * Feb. 16, 1988

[54] COLLAGEN MEMBRANES FOR MEDICAL USE

[75] Inventors: George Chu, Sunnyvale; John R. Daniels, Pacific Palisades, both of Calif.

[73] Assignee: Collagen Corporation, Palo Alto, Calif.

[*] Notice: The portion of the term of this patent subsequent to Jul. 15, 2003 has been disclaimed.

[21] Appl. No.: 825,812

[22] Filed: Feb. 4, 1986

Related U.S. Application Data

[63] Continuation-in-part of Ser. No. 685,350, Dec. 24, 1984, Pat. No. 4,600,533.

[51] Int. Cl.$^4$ .................. C07K 15/20; C07G 7/00; C08H 1/06
[52] U.S. Cl. ..................................... 530/356; 514/21; 514/801; 128/156; 128/DIG. 8
[58] Field of Search ................ 530/356; 128/82, 155, 128/156, DIG. 8; 428/473; 514/801, 21

[56] References Cited

U.S. PATENT DOCUMENTS

| 2,934,446 | 4/1960 | Highberger et al. | 530/356 |
| 4,140,537 | 2/1979 | Luck et al. | 530/356 |
| 4,242,291 | 12/1980 | Hughes et al. | 261/1 |
| 4,412,947 | 11/1983 | Cioca | 530/356 |
| 4,453,939 | 6/1984 | Zimmerman et al. | 604/368 |
| 4,600,533 | 7/1986 | Chu | 530/356 |

FOREIGN PATENT DOCUMENTS

0089152A1 3/1983 European Pat. Off. .
0092200A2 4/1983 European Pat. Off. .
74039174 9/1983 Japan .

Primary Examiner—Delbert R. Phillips
Assistant Examiner—Nathan M. Nutter
Attorney, Agent, or Firm—Ciotti & Murashige, Irell & Manella

[57] ABSTRACT

Collagen membranes with desired properties are prepared by using a variety of gel-forming techniques in combination with methods for converting the gels to solid forms. The properties of these membranes or other solid forms may be further altered by cross-linking the collagen preparation either after formation of the membrane or gel, or most preferably by mixing cross-linked collagen with solubilized collagen in the original mixture used to create the gel.

19 Claims, No Drawings

COLLAGEN MEMBRANES FOR MEDICAL USE

CROSS-REFERENCE TO RELATED APPLICATION

This application is a continuation-in-part of copending U.S. patent application Ser. No. 685,350, filed Dec. 24, 1984 and now U.S. Pat. No. 4,600,533.

TECHNICAL FIELD

The invention relates to the field of materials useful for repair of tissue and relevant to wound healing. More precisely, the invention relates to a collagen membranous material prepared by a novel process, which membranes are biocompatible, noninflamatory, and useful in the repair of tissue as artificial implants.

BACKGROUND ART

Numerous attempts have been made to obtain artificial membranes which can be used as substitutes for skin, blood vessels, ligaments, or other connective tissue. Many of these membranes utilize collagen, as collagen is the major component of connective tissue in general. An extensive literature exists with respect to methods for preparing such membranes, either of collagen alone, (see, for example, U.S. Pat. No. 4,412,947; Japanese Pat. No. 74/039174; and U.S. Pat. No. 4,242,291) or of collagen in combination with other materials (see, e.g., U.S. Pat. No. 4,453,939). Other membranes use combinations of materials such as glycoproteins with fibrinogen and thrombin (EPO Application Publication No. 92200, published Oct. 26, 1983), and a combination of keratin derived and glycosaminoglycan polymers (European Patent Publication No. 89152, published Sept. 21, 1983).

The properties and quality of the resulting membranes with respect to physical characteristics useful in the particular application intended, and their biological characteristics, such as biocompatibility, stability, and integration with surrounding tissue are determined by the nature of the material, e.g., the nature of the collagen used to form the membranes, and on the process used in their formation.

The membranes in the art have had variable success for their intended uses, which include cornea replacements, artificial skin, and wound healing. Many cause inflamation, and have less than optimum properties of flexibility, biological stability, and strength.

The present invention offers a process whereby desirable properties can be obtained in the resulting membrane through the use of nonimmunogenic collagen formed into a membranous material by a spectrum of processes which offer flexibility in the physical properties of the product, so as to permit these properties to be adapted to intended use. The membranous material can be used as a two-dimensional membrane, including membranes which can be shaped to form tubular vessels, shaped into a three-dimensional implant, or formed into a one-dimensional fiber.

DISCLOSURE OF THE INVENTION

The invention provides collagen membranes whose physical properties are designed to be suitable for uses in a variety of medical applications including blood vessel repair, uterus repair, reconstruction of lumen surfaces, tendon replacements, and artificial skin. The membranes may also be used as substrates for production of desired cell cultures in vitro. The properties of the membrane are determined by appropriate selection from a spectrum of preparation processes so as to obtain those characteristics appropriate for a selected use. Similar flexibility is available in the properties of the one- and three-dimensional constructs prepared by modification of, or additions to, the membrane preparation process. The resulting fibers are useful as replacement materials for tendons or ligaments, and may also be used for suturing: the three-dimensional blocks or solids provide implants for use in tissue repair or wound-gap closure.

Thus, in one aspect, the invention relates to collagenous membranous materials which are prepared by the general process of obtaining a gel from a solution of atelopeptide collagen, optionally mixing the solution with a suspension of cross-linked collagen, and converting the gel into membrane form. In another aspect the invention relates to fibers or solids prepared from the gel. In still another aspect, the invention relates to the general process itself, and to the specific methods used within the context of this general process to obtain two-dimensional membranes, fibers, and solids of desired properties.

The gel may be obtained from solubilized collagen or mixture by three alternative approaches. In one approach, the solution of collagen is treated with a precipitating buffer which insolublizes the collagen by raising the pH. In this approach, both collagen and buffer solutions are precooled almost to freezing, mixed, and then allowed to incubate at approximately room temperature to induce gel formation. In a second approach, the above mixture of collagen and buffer is centrifuged, rather than incubated without gravitational pressure, and the supernatant from the centrifugation is recovered and allowed to incubate at approximately room temperature. In a third approach, the solution of collagen is treated with an insolubilizing solution at ambient temperature, and the insolubilizing solution is designed to bring the resulting mixture to physiological pH and ionic strength. This mixture is then allowed to incubate at approximately 37° C. to create the gel. The third approach may be modified by degassing the mixture immediately upon mixing, and placing the degassed mixture into a mold before incubation.

The procedure in each of the three cases recited above may also be applied to formation of a gel which includes, in addition to the dissolved collagen, a suspension of a cross-linked form. The presence of this additional cross-linked substrate permits further variation in the properties of the membrane material which ultimately results from the method of the invention.

Inclusion of the cross-linked collagen in the starting material for the procedure set forth above for formation of the gel appears to be critical in the sense that obtaining cross-linking in the product by formation of the gel from solubilized collagen alone, followed by partial cross-linking, or carrying out cross-linking of the membranes after their formation from the gel appear to result in more brittle and less satisfactory products. If the gel formation procedure from solubilized collagen is modified by the aforementioned addition of cross-linked material, the third method recited is preferred, i.e., the solution of collagen (containing, in admixture, the desired cross-linked material) is treated with an insolubilizing solution at ambient temperature wherein the insolubilizing solution is designed to bring the mixture to physiological pH and ionic strength. The mixture is allowed to incubate at about 37° C. to create the gel. In a particularly preferred embodiment, the mixture is degassed before adding the insolubilizing solution.

The conversion of the gel to a membranous material may also be accomplished by two basic alternative approaches. In one approach, the gel is compressed, either by applied pressure or by absorbing the contained moisture to form a mat which is then dried. Using this method, in addition to obtaining two-dimensional membranes, a solid implant may be prepared directly by compressing the molded gel obtained from the modification of the gel formation process which employs degassing. A fiber product is obtained if the compression is applied around the circumference of a cylinder formed from the gel. In a second approach to membranous material formation, the gel is disrupted, the disrupted gel centrifuged to obtain a precipitate, and the precipitate cast into molds and dried. Depending on the dimensions and shape of the mold, either a two-dimensional membrane or a three-dimensional solid can be obtained.

MODES OF CARRYING OUT THE INVENTION

A. Preparation of Collagen in Solution (CIS)

The process of the invention starts with a collagen in solution, either alone, or in admixture with cross-linked fibrillar collagen. The CIS may be solubilized and purified from mammalian connective tissue, and has been prepared from bovine skin, porcine skin, and mammalian bone, as well as from a number of other sources. Purification processes are well known in the art. See, for example, U.S. Pat. No. 3,949,073, U.S. Pat. No. 4,066,083, and GB No. 1,565,340. Collagen can be readily solubilized in concentrations useful in the invention by disrupting the fibers in acid, as is well known in the art, and is dissolved at pH values between 1–4. Indeed, Collagen in Solution (CIS) is commercially available under the trademark Zygen ® from Collagen Corporation, Palo Alto, Calif.

Native collagen exists in a fibrillar form which results from the triple helical structure of the peptide chains. The helical structure is generated by virtue of repeating triplet sequences composed of glycine linked to two amino acids, commonly proline and hydroxyproline in the amino acid sequence. The regions of these triplet repeating units aggregate themselves into triple helical structures. In addition, all collagen chains contain regions at each end which do not have the triplet glycine sequence and are thus not helical. These regions are thought to be responsible for the immunogenicity associated with most collagen preparations, and are called telopeptides. The immunogenicity of a collagen preparation can, in large part, can be mitigated by removal of these telopeptides to produce "atelopeptide collagen". The removal is accomplished by digestion with proteolytic enzymes such as trypsin or pepsin. The nonhelical telopeptide regions are also required to form the cross-links which are responsible for stability of the fibrillar structure in the native material. Atelopeptide collagen must be cross-linked artificially, if it is desired to obtain this characteristic.

The collagen in solution which forms the starting material for the process of the invention is an atelopeptide collagen, preferably a dilute commerically available product such as Zygen ® CIS. Concentrations of collagen in the range of 2–4 mg/ml are suitable for use in the invention. This range is, of course, suggestive of suitable concentrations and not meant to represent an absolute limitation; any upper and lower limit is arbitrary in this context.

B. Preparation of Cross-Linked Collagen

As used herein, "cross-linked collagen" refers to an atelopeptide purified reconstituted collagen preparation which has been artificially cross-linked by chemical or radiation treatment or by other appropriate means to obtain sufficient cross-links so that the viscosity of the preparation is 700–3000 centipoise measured at 22° C. and a shear rate of 5000 sec$^{-1}$ when the collagen concentration in the suspension is in the 25–40 mg/ml range. Again, precise limits are arbitrary and this is illustrative of a useful range. Of course, the higher the degree of cross-linking, the less cross-linked form needs to be added to the composition to obtain a given set of properties.

To prepare the cross-linked form, solubilized collagen is first precipitated by neutralizing at room temperature to obtain a suspension and then cross-linked using standard procedures, including reactivity with chemical cross-linking reagents, such as formaldehyde, glutaraldehyde, glyoxal, and so forth, or with ionizing radiation such as gamma ray radiation. Heat and UV radiation can also be used, but are less efficient. The cross-linked material is then collected by centrifugation and washed with a suitable aqueous solution, such as physiological saline, and the concentration adjusted to a workable level of 20–70 mg/ml in the suspension.

In more detail, the cross-linking agent is a polyfunctional, and more usually bifunctional, compound which is used in concentration to produce a viscous, covalently cross-linked collagen before quenching with an agent which forms an innocuous, water-soluble adduct with the cross-linking agent. The concentration of the collagen in the suspension during the reaction, the concentration of cross-linking agent, and the duration of the cross-linking reaction are significant, but dependent on the nature of the cross-linking agent. The collagen concentration in the suspension is typically in the range of 0.1–10 mg/ml, more usually 1–5 mg/ml. Aldehydes are preferred as cross-linking agents, and suitable aldehydes include formaldehyde, glutaraldehyde, acid aldehyde, glyoxal pyruvic aldehyde, and aldehyde starch, but preferably glutaraldehyde. Amines are preferred quenching agents, in particular, glycine. The concentration of glutaraldehyde, if this is the selected cross-linker, is typically about 0.001%–0.1% by weight/volume, and the cross-linking reaction takes place over about one-half hour to one week. The reaction is carried out at about 10° C.–35° C. before adding the quenching agent in at least stochiometric proportions with the cross-linking agent, although an excess is preferred. One exemplary cross-linking protocol includes a collagen concentration of 3 mg/ml and 0.01% by weight glutaraldehyde for about 16 hours at 22° C. The cross-linked product is washed to remove unreacted cross-linker, self polymerization products formed by the cross-linker, and the unreacted quenching agent, if quenching is employed. A workable buffer is a sodium phosphate/sodium chloride buffer solution of approximately pH 7.

The washed product may be concentrated by ultrafiltration or centrifugation to a suitable protein concentration range, which is typically about 20–50 mg/ml, preferably about 25–40 mg/ml. The washed product should have an aldehyde content of less than about 20 ppm and a viscosity in the range of about 700–3000 cp at 22° C. for a suspension containing 25–40 mg/ml measured by an oscillating disc viscosimeter, which measures dynamic, not steady flow, viscosity (Nametre Company, Model 7.006PBD).

C. Formation of the Gel

The process of the invention for forming collagen membranes or related membranous materials, comprises, basically, two steps: the formation of a gel from a collagen in solution, and the conversion of the gel to the membrane or other desired form.

Each of these processes may be performed in a spectrum of temperature, gravitational, and ionic strength conditions, and the intermediate solutions may or may not be degassed, and the resulting product will have properties which vary accordingly. The temperature at which gel formation takes place may be between approximately 4° C. and approximately 37° C.; the ionic strength may vary between about 0.05 to about physiological ionic strength, and the gravitational field conditions may vary from $1 \times g$ to about $13000 \times g$. The exemplary processes set forth below typify the extremes of these variables, and it is understood that intermediate cases may also be useful, depending on the nature of the membrane desired. Degassing and molding prior to formation of the gel appears to result in a tougher product, which can be further manipulated to form a fiber. membrane or solid.

Three general approaches may be used, as is outlined above. In the first, CIS is cooled and mixed with precooled buffer at an ionic strength well below physiological, preferably about 0.05, and the mixture incubated at low temperature. In the second, the CIS is mixed with buffer at physiological ionic strength and temperature conditions and incubated at physiological temperature. In a third approach, the CIS is treated with buffer both cooled as in the first method, but subjected to gravitational pressure before incubating at room temperature.

The gel may optionally contain an arbitrary amount of previously cross-linked collagen material which is itself prepared from solubilized collagen. The relative amounts of cross-linked and noncross-linked collagen materials appear to determine the properties of the resulting membranes, as well as do the conditions for formation of the gel and of the membranous product. The formation of the gel and the conversion to membranous product utilizes the same set of options, whether or not the cross-linked material is included in the original composition.

Thus, in forming the gel, as the intermediate material to the final membranous product to include the cross-linked fibrillar collagen, the gelling procedure is conducted as outlined above, except that, in addition to the collagen in solution, a portion of the suspension containing the cross-linked form at the above-mentioned suspension concentration levels is mixed with the solubilized collagen. The ratio of the two components, based on the relative weights of the collagen contained in each, is quite broad, depending on the nature of the final product desired. For softer and more flexible compositions, a greater proportion of collagen in solution is used; for tougher membranes as final products, a greater concentration of the cross-linked form is used. For example, if the membranous final product is to be used as an artificial tendon to hold sutures or to form a tubular vessel held together by such sutures, a cross-linked collagen percentage by weight based on total collagen of about 40–80%, preferably around 50%, is preferred.

All compositions of membranes formed wherein the original mixture for gel formation contains both a suspension of cross-linked collagen and collagen in solution are expressed as a percentage by weight of cross-linked collagen to total collagen content. Thus, when a membrane is described as having 10% cross-linked collagen, the original components were supplied such that 10% of the total weight of collagen was contained in a cross-linked collagen suspension and 90% was supplied as soluble collagen in solution. The compositions of the invention may contain up to 95% cross-linked collagen.

D. Conversion to the Membrane

The conversion of the gel to a membrane may be effected in two basically different ways. One employs compressing the gel either by directly applying pressure or by application of an absorbent material to squeeze out liquid to form a more cohesive "mat", followed by drying at roughly atmospheric pressure, for example, in air. The second employs disrupting the gel matrix, centrifuging the disruptate to recover a precipitated collagen, homogenizing the precipitate into a paste, and casting the paste with a mold.

The nature of the properties of the resulting membrane depends greatly on which of these two conversion processes is used; the product of the compression process is flexible, translucent, and smooth, and forms a filmlike material with relatively high tensile strength when wetted. The product of disrupting the gel followed by concentration of the disruptate, is relatively brittle, semitransparent, and has a rough surface.

Either membrane, however, can be characterized as a random fibrillar network wherein the fibrils are approximately of the diameter 70–300 nanometers, and approximately $0.5-5\mu$ in length.

The inclusion of cross-linked collagen does not change the general description of these properties, except to toughen the product. The cross-linked material is embedded in the fibrillar network described.

In one embodiment of the compression process, the gel is squeezed in a suitable piston type device, such as, for example, the apparatus presently used to obtain cakes of tofu. This direct compression is conveniently conducted at approximately room temperature by using the collagen gel in situ in the medium in which it was prepared. The compression is applied using 1.1–3 atmospheres pressure, and continued until the volume is approximately less than 5% of the original gel. An alternative method to effect compression is to absorb the aqueous fraction from the gel by sandwiching the gel between highly absorbent materials, e.g., sterile guaze, fibrillar polyester, absorbent cotton and the like. This results in a similar product to that obtained in a press. The resulting flat collagen fiber mat is then dried in air or other appropriate atmosphere or at reduced pressure at a low temperature (less than about 37° C.) to obtain the desired membrane. It is also desirable to wash the remaining salts from the membrane. The washing can be effected by washing with water, and redrying, again at atmospheric pressure, at low temperature.

The process which utilizes disruption of the gel preferably is conducted by mechanically disrupting the matrix, such as with a spatula. followed by centrifugation at approximately $13000 \times g$ for about 20–30 minutes to obtain the precipitate. A workable range is $8,000 \times g - 13,000 \times g$ for 10 min–1 hour although times longer than 1 hour are also acceptable. In general, lower speeds need longer times of centrifugation. The precipitate is then homogenized sufficiently to form a pastelike material, at room temperature, and the paste is cast into a mold and allowed to set in at atmospheric pressure at low temperature (below about 37° C.). The dried material is then desalted, if desired, by washing in water, and redrying.

Cross-linking of the collagen in the resulting membranous material by application of cross-linking protocols to this product is optional, and can be effected by treating the membranous material with glutaraldehyde or other cross-linking agents to obtain the desired cross-links; however, as set forth above, this approach may result in a more brittle product. Procedures for this cross-linking are described above and are known in the art. In an exemplary procedure the material is treated with a solution containing 0.05-1% glutaraldehyde for 1-16 hours, and then quenched by addition of a glycine solution to a concentration of about 0.1-0.4M glycine. The cross-linking solution is then removed by washing.

E. Utility

The resulting materials may be employed in the soft tissue repair constructions ordinarily utilizing artificial membranes, such as burned skin replacements, tendon reconstruction, or wound repair. They may also be shaped into various forms and used in connection with hard tissue repair. The cast or compressed membranes may be reformed into three dimensional objects for implantation in replacing sections of bone by rolling into cylinders, or by stacking and cutting to shape. The membranes may also be used in their two dimensional configuration by successively packing the membranes into a defect, such as a cranial or peridontal cavity. In general, onlay-type repair may be done by stacking these membranes into the cavity.

Three dimensional implants are also obtainable directly from the gel by compression into an appropriate mold. In this method of construction, it is preferred that the mixture containing the CIS and precipitating buffer be degassed and molded prior to compression. (Degassing may be used in the related processes which result in membranes and fibers, also). The dense collagen fiber network which is formed by compression of the degassed, molded collagen gel is dried, desalted by washing, remolded before redrying, and , if desired, aged at elevated temperature to encourage residual cross-linking. In addition, fibers can be formed preferably directly from the gel before compression or disruption. The gel is wrapped in a porous, absorbent material and squeezed or rolled into the desired diameter fiber. The disrupted gel may also be used, but in this event fibers must be formed by casting and stretching, and the process is more cumbersome, leading to a less desirable product.

EXAMPLES

The following examples are intended to illustrate, but not to limit the invention. The first three examples represent alternative methods of forming the gel, combined with the compression method for forming a membrane; examples 4-6 represent similar gel forming methods, followed by membrane formation using a disruptate; all of these illustrations start with CIS alone. Examples 7 and 8 illustrate formation of cross-links in the resulting membranes whether the membranes are formed by compression or by disruption and precipitate recovery. Example 9 shows the use of degassed and molded mixtures in gel formation where the gel is used directly in forming a three dimensional implant. Example 10 shows the formation of a gel which includes a portion of cross-linked collagen, and Example 11 illustrates the conversion of this gel into a membrane. Example 12 illustrates additional embodiments of membranous material which includes cross-linked collagen.

EXAMPLE 1

90 ml Zygen ® (3 mg/ml bovine atelopeptide collagen, in HCl, pH1-4) CIS was cooled to 4° C., and mixed with 10 ml of precooled buffer containing 0.2 M $Na_2HPO_4$/0.09 M NaOH. The solution was mixed at 4° C., and incubated at room temperature for about 16-20 hours, i.e., overnight, for convenience. The resulting collagen gel was then placed in a press and compressed using constant pressure of about 1.5 atmospheres to a flat collagen fiber network. The resulting network was dried in air at room temperature, washed with water, and redried in air. The resulting collagen membrane was designated G-1.

EXAMPLE 2

90 ml of Zygen ® CIS at ambient temperature was mixed with 10 ml of room temperature buffer containing 0.2 M $Na_2HPO_4$/1.3 M NaCl/0.09 M NaOH, and the mixture incubated at 37° C. overnight. The resulting matrix was converted to a membrane as set forth in Example 1. The resulting membrane, G-2, is a smooth flexible translucent material.

EXAMPLE 3

90 ml of Zygen ® CIS was cooled to 4° C., and mixed rapidly with 10 ml cold (4° C.) buffer containing 0.2 M $Na_2HPO_4$/0.09 M NaOH, and transferred immediately to centrifuge bottles. The mixture was centrifuged at 8,000×g for 2 hours at about 20° C., and the supernatant recovered from the bottles. The supernate was incubated at 20° C. for overnight, resulting in the gel. The gel was converted into the membrane in a manner exactly similar to that set forth Example 1, and designated G-3.

EXAMPLE 4

90 ml Zygen ® CIS and 10 ml insolubilizing buffer were mixed at 4° C., and incubated to form a gel exactly as set forth in Example 1. The gel matrix was broken with a spatula, transferred to a centrifuge bottle, and centrifuged at approximately 13,000×g for 30 minutes. The resulting precipitate was recovered and homogenized into a paste form. The paste was cast into a mold and dried in air at 37° C., then washed with water and redried in air at 37° C. to give the membrane P-1.

EXAMPLE 5

Zygen ® CIS was treated with buffer to form a gel exactly as described in Example 2, and the gel then converted to a membrane using the procedure exactly as set forth in Example 4. The resulting membrane was designated P-2.

EXAMPLE 6

Zygen ® CIS was used to form a gel using the procedure as set forth in Example 3, and the resulting gel converted to a membrane as set forth in Example 4. The resulting membrane was designated P-3.

EXAMPLE 7

90 ml Zygen ® CIS at ambient temperature was mixed with 10 ml buffer which contained 0.2 M $Na_2H$-

PO$_4$/1.3 M NaCl/0.09 M NaOH, and the mixture incubated at 37° C. overnight. The resulting gel was compressed as set forth in Example 4, dried, and desalted by washing. The washed membrane was then cross-linked by treating with 0.1% glutaraldehyde dissolved in water at 20° C., and the cross-linked membrane washed and dried at low temperature to obtain membrane XG-2.

EXAMPLE 8

A gel was formed from 90 ml Zygen® CIS as described in Example 7, and the resulting gel broken with a spatula, transferred to a centrifuge bottle, and centrifuged at 13000×g for 30 minutes. The precipitate was recovered and homogenized to a paste. The paste was cast into a mold and dried in air at 37° C., and the resulting membrane washed with water. The washed membrane was then treated with a 0.1% solution of glutaraldehyde, as set forth in Example 7, and the cross-linked membrane washed and dried in to yield membrane XP-2.

EXAMPLE 9

The procedure for gel formation as set forth in Example 2 was modified by degassing and molding the pre-gel mixture. Before incubation, the mixture was degassed by reduced pressure and placed in a mold. After incubation at 37° for 16-20 hours, the molded gelatin was compressed at about 1.5 atm to obtain a dense fiber network, which was dried in air at 37° or less. The dried solid was desalted by washing, remolded, dried, and aged at an elevated temperature of about 40° C.-100° C. to increase residual cross-linking, to give the product designated "preformed G-2".

EXAMPLE 10

A. Preparation of Cross-Linked Collagen

Fibrous collagen was reconstituted from collagen in solution (a 3 mg/ml solution of atelopeptide bovine collagen in dilute aqueous HCl, pH 1-4) by adding 0.2 M disodium phosphate to the solution at 18°-20° C. to obtain a pH of 7.4, and allowing fibers to form for 1-2 hours. To 160 ml of the resulting fibrous collagen suspension, 1.62 ml of 1% aqueous glutaraldehyde at pH 3 was added. The glutaraldehyde solution was added gradually with stirring to obtain a final concentration of 0.01% glutaraldehyde, and the mixture was allowed to react for 16 hours at room temperature before quenching by the addition of 3 M glycine to 0.2 M. After a 1 hour quench time, the cross-linked collagen was washed 3 times with approximately 100 ml of a buffer which contains 0.02 M disodium phosphate, 0.13 M NaCl, pH 7.4, with centrifuging at 17,000×g for 5-7 minutes between each wash. The dynamic viscosity of the collagen was measured by an oscillating disc device (Nametre Company, Model 7.006PBD) measured at a shear rate of about 5,000 sec$^{-1}$, and found to be approximately 700 cp at 22° C. After the final wash and centrifugation, the collagen was resuspended in the above buffer to obtain a protein concentration of about 30 mg/ml.

B. Preparation of the Gel

Ten ml of the suspension of A was mixed with 90 ml Zygen® CIS (3 mg/ml) and the thoroughly mixed components were degassed under a vacuum. To the degassed mixture was added 10 ml of room temperature buffer containing 0.2 M Na$_2$PO$_4$/1.3 M NaCl/0.09 M NaOH, and the mixture was incubated at 37° C. overnight. The resulting gel contains 53% cross-linked collagen by weight.

EXAMPLE 11

The gel of Example 10 was placed in a press and compressed using constant pressure of about 1.5 atmospheres to obtain a flat collagen fiber network. The resulting network was dried in air at room temperature, washed with water, and redried in air. The resulting collagen membrane was designated GX-2.

EXAMPLE 12

The cross-linked collagen preparation prepared as in A of Example 10 is used in a ratio of 1:9 to collagen in solution to obtain a gel (prepared as in Example 1) and subjected to the process of Example 1 to obtain a membrane designated GX-1 or of Example 3 to obtain a membrane designated GX-3. Similarly, PX-1, PX-2, and PX-3 are prepared as set forth in Examples 4, 5, and 6, but using a 1:9 mixture of cross-linked to CIS collagen as the starting material.

Variations in the percentage of cross-linked collagen in the product are also obtained by varying the proportions of the suspension of Example 10A to the CIS.

We claim:

1. A process for preparing a collagen membranous material which comprises compressing a collagen gel matrix to form a fiber network, and drying said network, wherein the compression is conducted by absorbing the aqueous fraction from the gel.

2. The process of claim 1 wherein the compression is conducted by absorbing the aqueous fraction from the gel by sandwiching the gel between absorbent materials.

3. The process of claim 1 which further includes the steps of washing said network, and redrying.

4. The process of claim 1 which further indicates the step of cross-linking the membranous material after said compression step.

5. A process to prepare a gel useful for conversion to a collagen membranous material which comprises
cooling atelopeptide collagen-in-solution to approximately 4° C.,
treating the cooled solution with a buffer solution precooled to approximately 4° C., to obtain a mixture with a pH of approximately 7 and an ionic strength of approximately 0.05, and
incubating the mixture at about 20° C. for about 16-20 hours.
wherein the collagen in solution is mixed with a suspension of cross-linked collagen to obtain a percentage of cross-linked collagen of 10% to 95%.

6. A process to prepare a gel useful for conversion to a collagen membranous material which comprises
mixing, at ambient temperature, atelopeptide collagen-in-solution with sufficient salt/buffer solution to obtain a mixture with a pH of approximately 7 and of approximately physiological ionic strength, and
incubating the mixture at about 37° C. for 16-20 hours,
wherein the collagen in solution is mixed with a suspension of cross-linked collagen to obtain a percentage of cross-linked collagen of 10% to 95%.

7. A process to prepare a gel useful for conversion to a collagen membranous material which comprises precooling atelopeptide collagen-in-solution to about 4° C., mixing the cooled collagen in solution with a buffer solution, precooled to about 4° C. to obtain a mixture with a pH of approximately 7 and ionic strength of about 0.05, and centrifuging the mixture at about 8,000×g to 13,000×g for 1-2 hours at about 4°-25° C., immediately after mixing to obtain a supernatant, recovering the supernatant, and incubating the supernatant at about 20° C. for 16-20 hours, wherein the collagen in solution is mixed with a suspension of cross-linked collagen to obtain a percentage of cross-linked collagen of 10% to 95%.

8. The process of claim 5 wherein the gel is converted to the collagen membranous material by compression.

9. The process of claim 8 wherein the compression is conducted by absorbing the aqueous fraction from the gel.

10. The process of claim 6 wherein the gel is converted to the collagen membranous material by compression.

11. The process of claim 10 wherein the compression is conducted by absorbing the aqueous fraction from the gel.

12. The process of claim 7 wherein the gel is converted to the collagen membranous material by compression.

13. The process of claim 12 wherein the compression is conducted by absorbing the aqueous fraction from the gel.

14. A collagen gel prepared by the process of claim 5.

15. A collagen gel prepared by the process of claim 6.

16. A collagen gel prepared by the process of claim 7.

17. A collagen membranous material prepared by the process of claim 8.

18. A collagen membranous material prepared by the process of claim 10.

19. A collagen membranous material prepared by the process of claim 12.

* * * * *